US011370848B2

(12) United States Patent
Torri et al.

(10) Patent No.: US 11,370,848 B2
(45) Date of Patent: *Jun. 28, 2022

(54) CARBOXYLATED DERIVATIVES OF GLYCOSAMINOGLYCANS AND USE AS DRUGS

(71) Applicant: Novahealth Biosystems, LLC, Waunakee, WI (US)

(72) Inventors: Giangiacomo Torri, Milan (IT); Annamaria Naggi, Legnano (IT)

(73) Assignee: Novahealth Biosystems, LLC, Waunakee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/798,065

(22) Filed: Feb. 21, 2020

(65) Prior Publication Data
US 2020/0190224 A1 Jun. 18, 2020

Related U.S. Application Data

(63) Continuation of application No. 15/034,555, filed as application No. PCT/EP2014/072676 on Oct. 22, 2014, now Pat. No. 10,822,430.

(30) Foreign Application Priority Data

Nov. 6, 2013 (IT) ............... LO2013A0006

(51) Int. Cl.
*C08B 37/00* (2006.01)
*C08B 37/08* (2006.01)

(52) U.S. Cl.
CPC ...... *C08B 37/0063* (2013.01); *C08B 37/0069* (2013.01); *C08B 37/0072* (2013.01); *C08B 37/0075* (2013.01); *C08B 37/0078* (2013.01)

(58) Field of Classification Search
CPC .... A61P 7/00; A61P 3/10; A61P 35/00; A61P 19/02; A61P 9/10; A61P 1/00; A61P 13/12; A61P 35/04; A61P 17/06; C08B 37/0075; C08B 37/0078; C08B 37/0063; C08B 37/0072; C08B 37/0069
USPC ......................................................... 536/21
See application file for complete search history.

(56) References Cited

U.S. PATENT DOCUMENTS 3,679,795 A * 7/1972 De Somer ............... C08B 31/18
514/25

FOREIGN PATENT DOCUMENTS

| CN | 1531555 A | 9/2004 | | |
|---|---|---|---|---|
| CN | 1547477 | 12/2010 | | |
| GB | 1295666 | 11/1972 | | |
| JP | 4-502928 | 5/1992 | | |
| JP | 2005506326 | 3/2005 | | |
| WO | WO 90/04607 | 5/1990 | | |
| WO | WO 92/15188 | 10/1992 | | |
| WO | WO 01/07486 | 2/2001 | | |
| WO | WO 01/55221 | 8/2001 | | |
| WO | WO 01/55221 A1 | * 8/2001 | ............. | C08B 37/10 |
| WO | WO 03/022291 | 3/2003 | | |

OTHER PUBLICATIONS

Claes et al, Journal of Virology, 1970, 5(3), 313-320.*
Casu et al, Pathophysiol Haemost Thromb Aug. 2007, 36, 195-203.*
Graham-Rowe, D., Multiple Myeloma Outlook, Nature, Dec. 15, 2011, pp. S34-S35, vol. 480.
Fux, Liat et al., Heparanase: Busy at the cell surface, Trends Biochem Sci., Oct. 2009, pp. 511-519, vol. 10.
Sanderson, Ralph et al., Syndecan-1: A dynamic regulator of myeloma microenvironment, Clin Exp Metastasis, 2008, pp. 149-159, vol. 25.
Ilan, Neta et al., Regulation, function and clinical significance of heparanase in cancer metastasis and angiogenesis, Science Direct: The International Journal of Biochemistry & Cell Biology, 2006, pp. 2018-2039, vol. 38.
Casu, Benito et al., Non-Anticoagulant Heparins and Inhibition of Cancer, Pathophysiology of Haemostasis and Thrombosis, Aug. 2007, pp. 195-203, vol. 36.
Vlodavsky, Israel et al., Haparanase: Structure, Biological Functions, and Inhibition by Heparin-Derived Mimetics of Heparan Sulfate, Current Pharmaceutical Design, 2007, pp. 2057-2073, vol. 13.
Naggi, Annamaria et al., Modulation of the Heparanase-inhibiting Activity of Heparin through Selective Desulfation, Graded N-Acetylation, and Glycol Splitting, JBC Papers in Press, Jan. 12, 2005, pp. 12103-12113, vol. 280.
Casu, Benito et al., Structure and Active Domains of Heparin, Chemistry and Biology of Heparin and Heparan Sulfate, 2005, pp. 1-28, Elsevier Ltd.
Casu, Benito et al., Structure and biological interactions of heparin and heparan sulfate, Advances in Carbohydrate Chemistry and Biochemistry, 2001, pp. 159-206, vol. 57, Academic Press, An Elsevier Science Imprint.

(Continued)

*Primary Examiner* — Ganapathy Krishnan
(74) *Attorney, Agent, or Firm* — Reinhart Boerner Van Deuren P.C.

(57) ABSTRACT

A glycosaminoglycan derivative endowed with heparanase inhibitory activity and antitumor activity, bearing carboxylate groups in positions 2 and 3 of at least part of the glycosaminoglycan residues, and to the process for preparing the same. The glycosaminoglycan derivatives of the present invention are generated starting from natural or synthetic glycosaminoglycans, preferably heparin or low molecular weight heparin, optionally 2-O- and 2-N-desulfated by two steps of oxidation. By the first oxidation, adjacent dials and optionally adjacent $OH/NH_2$ of the glycosaminoglycan residues are converted to aldehydes and by the second oxidation said dialdehydes are converted to carboxylate groups. The first oxidation preferably leads to the cleavage of C2-C3 linkage of the ring of oxidable residues. The invention relates to a process for the preparation of said glycosaminoglycan derivatives and to their use as active ingredients of medicaments.

18 Claims, 3 Drawing Sheets

(56) References Cited

OTHER PUBLICATIONS

Zacharski, L.R. et al, Heparin as an anticancer therapeutic, Expert Opinion on Investigational Drugs, Jul. 2008, pp. 1029-1037, vol. 17, London, UK.

Yang, Yang et al., The syndecan-1 heparan sulfate proteoglycan is a viable target for myeloma therapy, Blood, Sep. 15, 2007, pp. 2041-2048, vol. 110 No. 6, The American Society of Hematology.

Naggi, Annamaria et al., Glycol-Splitting as a Device for Modulating Inhibition of Growth Factors and Heparanase by Heparin and Heparin Derivatives, Chemistry and Biology of Heparin and Heparan Sulfate, 2005, pp. 461-481, Elsevier Ltd., Amsterdam.

Chemical Abstract Registry No. 53260-52-9; Nov. 16, 1984.

Chen, Jin-Lian et al., Effect of non-anticoagulant N-Desulfated heparin on expression of vascular endothelial growth factor, angiogenesis and metastasis of orthotopic implantation of human gastric carcinoma, World Journal of Gastroenterology, Jan. 21, 2007, pp. 457-461, vol. 13, The WJG Press.

Zhou, Tong et al., Effect of N-desulfated heparin on hepatic/renal ischemia reperfusion injury in rats, World Journal of Gastroenterology, 2002, pp. 897-900, vol. 8, The WJG Press.

Naggi, Annamaria et al., Toward a Biotechnological Heparin through Combined Chemical and Enzymatic Modification of the *Escherichia coli* K5 Polysaccharide, Seminars in Thrombosis and Hemostasis, Oct. 2001, pp. 437-443, vol. 27, No. 5, Thieme Medical Publishers, Inc., New York.

Inoue, Yuko et al., Selective N-Desulfation of Heparin with Dimethyl Sulfoxide Containing Water or Methanol, Carbohydrate Research, 1976, pp. 87-95, vol. 46, Elsevier Scientific Publishing Company, Amstrerdam—Belgium.

Naggi, Annamaria et al., Generation of anti-factor Xa active, 3-O-sulfated glucosamine-rich sequences by controlled desulfation of oversulfated heparins, Carbohydrate Research, Dec. 7, 2001, pp. 283-290, vol. 336 No. 4, Elsevier Science Ltd.

Rej Rabindra N. et al., Base-catalyzed conversation of the a-L-iduronic acid 2-sulfate unit of heparin into a unit of a-L-galacturonic acid, and related reactions, Carbohydrate Research, Apr. 25, 1990, pp. 437-447, vol. 200, Elsevier Science Publishers B.V., Amsterdam—Netherlands.

Casu, Benito et al., Undersulfated and Glycol-Split Heparins Endowed with Antiangiogenic Activity, Journal of Medicinal Chemistry, Feb. 12, 2004, pp. 838-848, vol. 47 No. 4, American Chemical Society, Washington D.C.

Bisio, Antonella et al., High-Performance Liquid Chromatographic/Mass Spectrometric Studies on the Susceptibility of *Heparin* Species to Cleavage by Heparanase, Seminars in Thrombosis and Hemostasis, Jul. 2007, pp. 488-495, vol. 33, No. 5, Thieme Medical Publishers, Inc. New York.

Hammond, Edward et al., Development of a colorimetric assay for heparanase activity suitable for kinetic analysis and inhibitor screening, Analytical Biochemistry, Jan. 1, 2010, pp. 112-116, vol. 396 Issue 1, Elsevier.

Vlodavsky, Israel et al., Current Protocols in Cell Biology, 1999, pp. 1-11, vol. 1, John Wiley & Sons, Inc., United States of America.

Heparin-Wikipedia; 21 pages, Aug. 22, 2019; https://en.wikipedia.ord/wiki/Heparin.

Benito Casu et al., "A conductimetric method for the determination of sulphate and carboxyl groups in heparin and other mucopolysaccharides", Dec. 31, 1975, pp. 168-176, Carbohydrate Research, vol. 39.

Fransson et al.; Relationship between anticoagulant activity of heparin and susceptibility to periodate oxidation; Jan. 1, 1979; pp. 119-123; FEBS Letters, Elsevier, Amsterdam, NL, vol. 97, No. 1.

Lapierre F et al., "Chemical Modifications of Heparin that Diminish its Anticoagulant but Preserve its Heparanase-Inhibitory, Antigostatic, Anti-Tumor and Anti-Metastatic Properties," Glycobiology, Oxford University Press, US, vol. 6, No. 3, Jan. 1, 1996, pp. 355-366.

Claes P et al., "Polyacetal Carboxylic Acids: A New Group of Antiviral Polyanions," Journal of Virology, the American Society for Microbiology, US, vol. 5, No. 3, Mar. 1, 1970, pp. 313-320.

Tommasina Coviello et al., "Scleroglucan: A Versatile Polysaccharide for Modified Drug Delivery," Molecules, vol. 10, No. 1, Jan. 31, 2005, pp. 6-33.

Scott et al, Histochemie, 1968, 14, 215-220.

U.S. Appl. No. 15/034,555, filed May 5, 2016.

Y. Li et al.; "Study on anti-metastasis of herapin derivatives as ligand antagonist of p-selectin"; Biomedicine and Pharmacotherapy vol. 64, No. 10, Dec. 2010; pp. 654-658.

Min Wei et al.; "Effects of the modification of herapin 6-Carboxyl Group on inhibitive activity of p-selectin-mediated A375 cells adhesion"; Progress in Biochemistry and Biophysics vol. 33, No. 1; Jan. 2006; pp. 72-76.

\* cited by examiner

CARBOXYLATED DERIVATIVES OF GLYCOSAMINOGLYCANS AND USE AS DRUGS

CROSS-REFERENCE TO RELATED PATENT APPLICATIONS

This patent application is a continuation of co-pending U.S. patent application Ser. No. 15/034,555, filed May 5, 2016, which is a National Stage Entry of PCT/EP2014/072676, filed Oct. 22, 2014, which claims priority to Italian Application No. LO2013A000006, filed Nov. 6, 2013, the entire teachings and disclosure of which are incorporated herein by reference thereto.

BRIEF SUMMARY OF THE INVENTION

The invention relates to glycosaminoglycan derivatives, endowed with heparanase inhibitory activity and antitumor activity, bearing carboxylate groups in positions 2 and 3 of at least part of the glycosaminoglycan residues, and to the process for preparing the same.

The glycosaminoglycan derivatives of the present invention are generated starting from natural or synthetic glycosaminoglycans, optionally modified chemically or enzymatically. In particular, said glycosaminoglycan derivatives are obtainable by two steps of oxidation of the glycosaminoglycan. By the first oxidation (a), preferably by periodate, adjacent diols and optionally adjacent OH/$NH_2$ of the glycosaminoglycan residues are converted to aldehydes and by the second oxidation (b) said dialdehydes are converted to carboxylate groups. According to the present invention, preferably from 10% to 100%, more preferably from 25% to 100%, of 2-O-non-sulfated residues and optionally 2N-, 3-O-non sulfated residues of a glycosaminoglycan are oxidized in the first oxidation step (a), under conditions effective to convert adjacent diols and optionally adjacent OH/$NH_2$ to aldehydes.

The first oxidation preferably leads to the cleavage of $C_2$-$C_3$ linkage of the ring of oxidable residues. Preferably, the glycosaminoglycan is a natural or synthetic glycosaminoglycan, optionally 2-O- and/or 2-N-desulfated, having a sulfation degree ($SO_3$—/COO— molar ratio) of from 0.8 to 2.8, preferably of from 0.9 to 2.5. The sulfation degree ($SO_3$—/COO— molar ratio) is herein intended as determined by conductimetric titration according to Casu B. and Gennaro U., 1975, Carbohydr Res 39, 168-176. The di/tricarboxylated glycosaminoglycan derivatives obtainable by the inventive process disclosed above show a carboxyl increment of from 1.2 to 2.2, wherein the carboxyl increment is calculated as the ratio of the sulfation degree ($SO_3$—/COO— molar ratio) of the starting material to the sulfation degree ($SO_3$—/COO— molar ratio) of the di/tricarboxylated derivative, determined by conductimetric titration as herein defined. More specifically, the sulfation degree of the starting glycosaminoglycan is determined on a sample of the glycosaminoglycan intermediate obtained by the first oxidation step (a), after reduction by $NaBH_4$.

Preferably, the glycosaminoglycan derivatives of the present invention are obtained starting from natural heparins from any animal and organ source, or from synthetic heparins, optionally chemically or enzymatically modified. More preferably, the starting material is unfractionated heparin, low-molecular-weight heparins (LMWHs, which have a molecular weight of from 3,500 to 8,000 Da.), heparan sulfate (HS) or derivatives thereof. Most preferred are glycosaminoglycan derivatives obtainable from unfractionated heparins or from LMWHs, optionally 2-O- and/or 2-N-desulfated.

The invention further relates to a process for the preparation of said glycosaminoglycan derivatives and further to their use as active ingredients of medicaments, optionally in combination with known established drugs or treatments. In particular, the present invention is directed to said glycosaminoglycan derivatives for use as medicaments for the treatment of pathological conditions, such as multiple myeloma and other neoplasias (i.e. sarcomas, carcinomas, hematological malignancies), including their metastatic forms.

Furthermore, the invention relates to the use of said glycosaminoglycan derivatives in any therapeutic indication gaining benefit from the inhibition of heparanase (i.e. diabetic nephropathy, inflammatory bowel disease, colitis, arthritis, psoriasis, sepsis, atherosclerosis). The invention also relates to pharmaceutical compositions comprising said di/tricarboxylated glycosaminoglycan derivatives, in particular to pharmaceutical compositions comprising di/tricarboxylated heparin and low molecular weight heparin (LMWH) derivatives, as active agent. Optionally, said pharmaceutical compositions further comprise at least one different active agent, preferably at least one different antitumoral agent.

BACKGROUND OF THE INVENTION

Multiple myeloma is the second most prevalent hematologic malignancy and accounts for over 10% of all hematologic cancer in Unites States, with around 20,000 new cases each year and a mortality greater than 50% (Graham-Rowe D., 2011, Multiple myeloma outlook. Nature 480, s34-s35).

Over the last few years, promising therapies have been developed, such as the administration of proteasome inhibitor (Velcade), bisphosphonates and thalidomide among others. The effectiveness of these agents is, at least in part, due to their impact on the myeloma tumor microenvironment.

Although efficacy of said agents against myeloma has been demonstrated, the need remains for new and improved drugs for treating myeloma and other tumors.

Heparanase is an endo-13-glucuronidase that cleaves heparan sulfate (HS) of HS-proteoglycans, such as syndecan-1, thereby releasing HS-bound growth factors.

In humans, there appears to be a single dominant functional heparanase enzyme capable of cleaving HS. Heparanase is expressed in most human tumors, where it significantly increases both the angiogenic and the metastatic potential of tumor cells. Elevated heparanase levels have been in fact correlated with advanced progression and metastasis of many tumor types. For example, high level of heparanase is associated with a shorter post-operative survival time of patients. A direct role of heparanase in tumor metastasis has been demonstrated in Vlodaysky's and Sanderson's laboratory, where our novel inhibitors have been tested.

In addition to its enzymatic functions, that include release of HS-bound growth factors and degradation of the extracellular matrix (ECM), heparanase has also a non-enzymatic function that may impact tumor behavior and microenvironment. Sanderson's group pioneered the study of heparanase and syndecan-1 in myeloma, establishing that heparanase acts as a master regulator of aggressive tumor phenotype in myeloma. This occurs by promoting the up-regulation of VEGF and MMP-9, that together stimulate tumor growth, metastatic and osteolytic bone destruction. It was in fact demonstrated in vivo that heparanase promotes the growth of myeloma tumors and spontaneous metastasis to bone and that heparanase expression by tumor cells fuels rampant osteolysis, at least partially due to up-regulation of RANKL expression. The osteolysis promoting effect of heparanase may be of great importance because bone-bound growth factors are released when bone is degraded. In addition, osteoclasts can release tumor growth promoting factors such as HGF. Together these factors may help establish niches within the bone marrow that support tumor cell homing and subsequent growth (Fux, L. et al., 2009, "Heparanase: busy at the cell surface." Trends Biochem Sci, 34 (10): 511-519; Sanderson R. D. and Yang Y., 2008, "Syndecan-1: a dynamic regulator of the myeloma microenvironment." Clin Exp Metastasis 25:149-59; Ilan N. et al., 2006, "Regulation, function and clinical significance of heparanase in cancer metastasis and angiogenesis." Int J Biochem Cell Biol, 38: 2018-2039). Inhibition of heparanase is thus a feasible target of myeloma therapy, supported by the fact that there is a single enzymatically active heparanase in humans and by the fact that its expression in normal tissues is rare. Furthermore, it has been shown that heparanase knock-out mice are viable and exhibit no visible disorders. This indicates that little or no side effect can derive from a heparanase inhibition strategy (Casu B., et al. 2008. Non-anticoagulant heparins and inhibition of cancer. Pathophysiol Haemost Thromb. 36: 195-203; Vlodaysky I., et al. 2007. Heparanase: structure, biological functions, and inhibition by heparin-derived mimetics of heparan sulfate. Curr Pharm Des. 13: 2057-2073; Naggi A., et al. 2005. Modulation of the Heparanase-inhibiting Activity of Heparin through Selective Desulfation, Graded N-Acetylation, and Glycol Splitting. J. Biol. Chem. 280: 12103-12113).

Heparin is a linear polydisperse sulfated polysaccharide of the glycosaminoglycan family, endowed with anticoagulant and antithrombotic activity. The saccharidic chains of heparin consist of alternating uronic acid and D-glucosamine. The major repeating unit is 2-O-sulfated L-iduronic acid (IdoA2S)a(1-4) and N-, 6-O-disulfated D-glucosamine (GlcN6S). Minor constituents are non-sulfated L-iduronic and D-glucuronic acid, along with N-acetyl D-glucosamine and N-, 3-O-, 6-O-trisulfated D-glucosamine (Casu B., 2005. "Structure and active domains of heparin." In: Chemistry and biology of heparin and heparan sulfate. Amsterdam: Elsevier. 1-28; Casu B. and Lindahl U., 2001, "Structure and biological interactions of heparin and heparan sulfate." Adv Carbohydr Chem Biochem, 57: 159-206). Heparin, which is structurally similar to HS, can efficiently inhibit heparanase, but its use of heparin at high doses in a heparanase inhibition strategy is however impossible due to its anticoagulant activity.

Interestingly, low molecular weight heparins (LMWHs), which are more bioavailable and less anticoagulant than heparin, appear to prolong survival of patients with cancer, probably through direct effect on tumor growth and metastasis. This may be due, at least in part, to inhibition of heparanase enzyme activity (Zacharski L. R., and Lee, A. Y. 2008. Heparin as an anticancer therapeutic. Expert Opin Investig Drugs 17:1029-1037).

Effective inhibitors of the enzymatic activity of heparanase have been selected in the prior art by studying heparanase inhibition by non-anticoagulant heparins, most of which contain non-sulfated uronic acid residues modified by opening of the glucosidic ring by cleavage of the linkage between carbons 2 and 3 of a glycosaminoglycan residue (glycol-splitting). Said inhibitors differ in their 0-sulfation patterns, degree of N-acetylation and glycol-splitting of both pre-existing non-sulfated uronic acid residues and those generated by graded 2-O-desulfation (Naggi A., 2005. "Glycol-splitting as a device for modulating inhibition of growth factors and heparanase inhibition by heparin and heparin derivative." In: Chemistry and Biology of Heparin and Heparan Sulfate. Amsterdam: Elsevier 461-481; Yang Y. et al., 2007, "The syndecan-1 heparan sulfate proteoglycan is a viable target for myeloma therapy." Blood, 110:2041-2048).

In particular, the terms "glycol split" (gs) conventionally refers to polysaccharides that present opening of some monosaccharide residues due to the break (glycol splitting) of one linkage between two adjacent carbons, each bearing an hydroxyl group. A first generation glycol split heparins, i.e. the so-called "reduced oxyheparins" (RO-heparins), consisted of unmodified polysulfated blocks occasionally interrupted by glycol split residues, corresponding to non-sulphated glucuronic acid/iduronic acid residues that were present along the original chain, first oxidized to dialdehydes and then reduced to alcohols (Naggi A., 2005, "Glycol-splitting as a device for modulating inhibition of growth factors and heparanase inhibition by heparin and heparin derivative." In: Chemistry and Biology of Heparin and Heparan Sulfate. Amsterdam: Elsevier 461-481).

WO 01/55221 discloses glycosaminoglycans with a 2-O-desulfation degree not greater than 60% of the total uronic acid units. Said glycosaminoglycans are devoid of anticoagulant activity and show antiangiogenic activity based on the inhibition of FGFs. No activity was foreseen for inhibition of heparanase.

US 2008/0051567 discloses a compound corresponding to a 100% N-acetylated and 25% glycol split heparin, exerting little or no anticoagulant activity or release of growth factors from the extracellular matrix. Said compound was found to inhibit heparanase, tumor growth, angiogenesis and inflammation in experimental animal models, including Sanderson's model of myeloma (Yang Y., et al. 2007. The syndecan-1 heparan sulfate proteoglycan is a viable target for myeloma therapy. Blood 110:2041-2048).

Despite that, the need remains for providing improved compounds with higher heparanase affinity, higher selectivity and improved bioavailability, being suitable for treating heparanase-related pathologies, such as myeloma and other tumors.

DETAILED DESCRIPTION OF THE INVENTION

Figure 1:
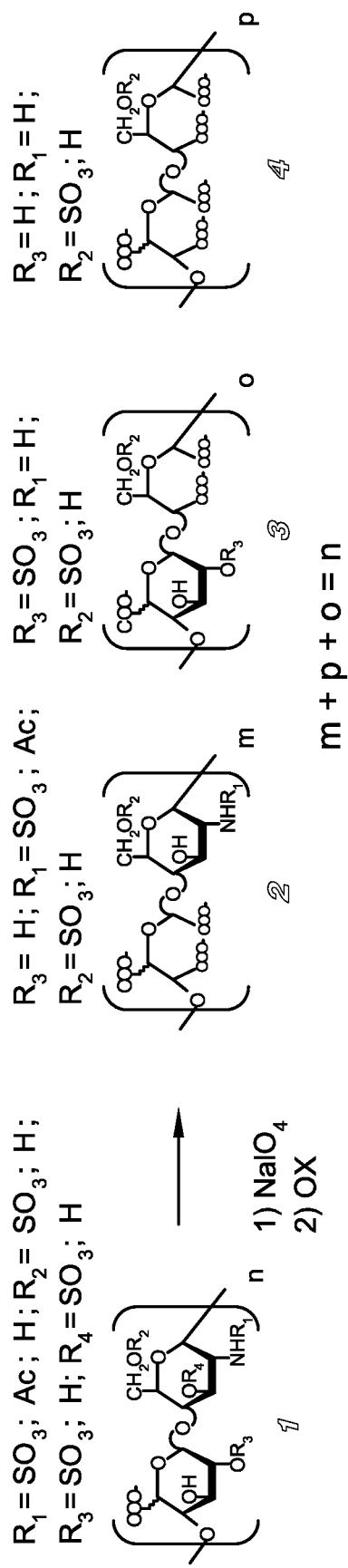
FIG. 1: prevalent structures generated by the process of the present invention. (1) disaccharidic unit of a glycosaminoglycan polymer comprising one uronic acid (iduronic and/or glucuronic) and one glucosamine (2-N-acetylated, 2-N-unsubstituted and/or 2-N-sulfated), in which the hydroxyl groups ($R_3$ and $R_4$) can each or both be substituted by a sulphate group or non-substituted. (2, 3, 4) representative structures (new entities) generated by oxidative cleavage of the ring of 2-non-sulfated heparin residues, followed by further oxidation to tri- or di-carboxylated residues.
Figure 2:
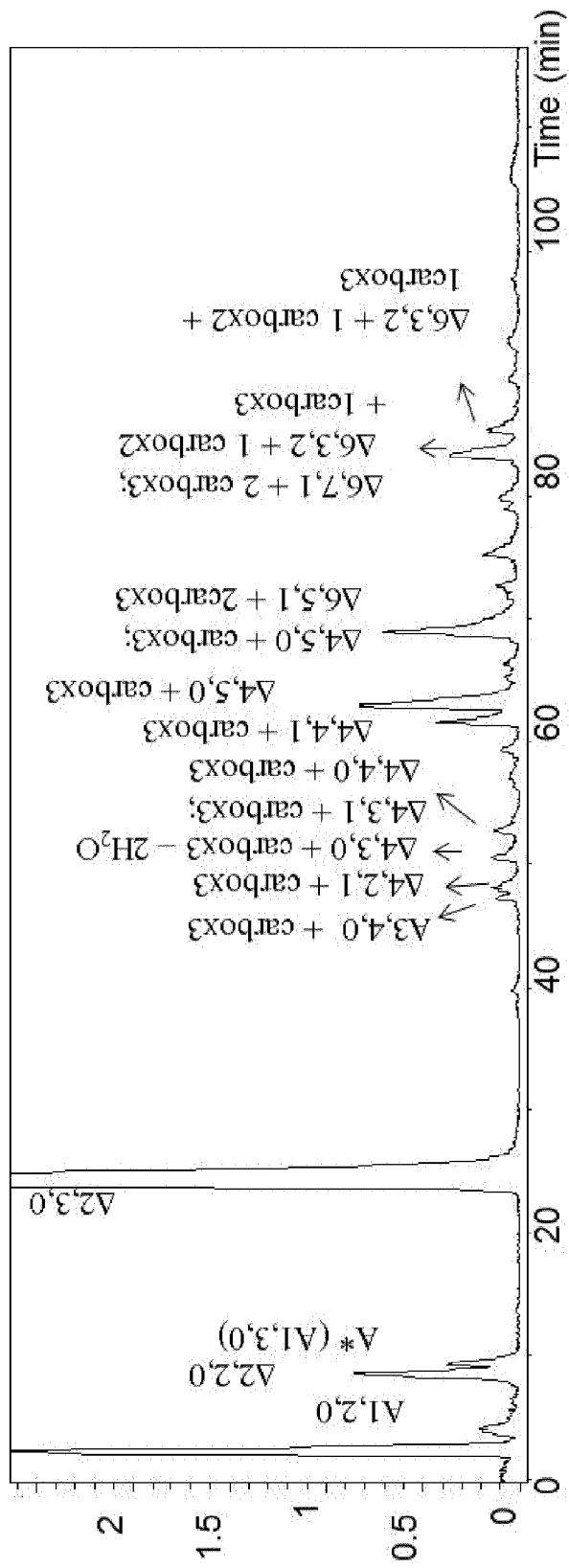
FIG. 2: one example of chromatogram obtained with MS detection. The presence of peaks corresponding to oligosaccharides containing the uronic acid di- or tri-carboxylate residues, attributed by the measured values of molecular weight, are highlighted respectively by the code "+carbox2" or "+carbox3" in the graph.
Figure 3:
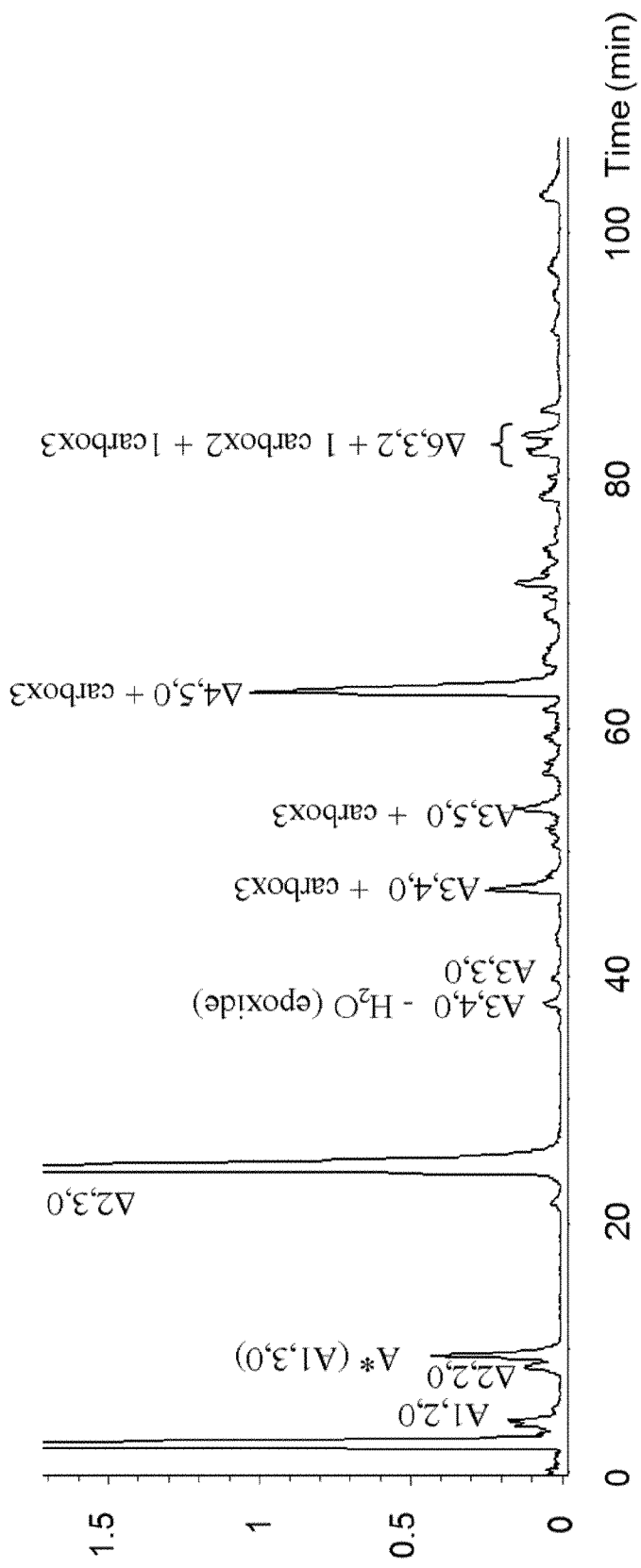
FIG. 3: one example of chromatogram obtained with MS detection. The presence of peaks corresponding to oligosaccharides containing the uronic acid di- or tri-carboxylate residues, attributed by the measured values of molecular weight, are highlighted respectively by the code "+carbox2" or "+carbox3" in the graph.

The present invention relates to a novel class of chemically modified glycosaminoglycan derivatives, endowed with heparanase inhibitory activity. In particular it relates to carboxylated glycosaminoglycan derivatives, wherein at least part of the residues are split residues bearing three carboxylate groups (or two, if the split residue is a glucosamine).

The glycosaminoglycan derivatives of the present invention are preferably heparin derivatives, designed as "di/tricarboxylated heparins", which strongly inhibit the heparan sulfate degrading activity of heparanase. The chemical modifications made to heparin, modifying the residue of glucuronic acid included in the binding site for ATIII, abolish the heparin anticoagulant activity, enabling the use of high doses.

The glycosaminoglycan derivatives of the present invention are obtainable by oxidation, preferably by periodate, of 2-non-sulfated residues of a glycosaminoglycan under conditions effective to convert adjacent diols and optionally adjacent $OH/NH_2$ of the glycosaminoglycan to aldehydes, followed by oxidation of the oxidized glycosaminoglycan under conditions to convert said dialdehydes to carboxylate groups. In particular, the glycosaminoglycan derivatives of the present invention are preferably obtainable starting from a glycosaminoglycan having a sulfation degree ($SO_3$—/COO— molar ratio) of from 0.8 to 2.8, preferably of from 0.9 to 2.5. The sulfation degree ($SO_3$—/COO— molar ratio) is herein intended as determined by conductimetric titration according to Casu B. and Gennaro U., 1975, Carbohydr Res 39, 168-176. The di/tricarboxylated glycosaminoglycan derivatives obtainable by the inventive process disclosed above show a carboxyl increment of from 1.2 to 2.2, wherein said carboxyl increment is calculated as the ratio of the sulfation degree ($SO_3$—/COO— molar ratio) of the starting material, after the first oxidation step, to the sulfation degree ($SO_3$—/COO— molar ratio) of the di/tricarboxylated derivative, determined by conductimetric titration as herein defined. More specifically, the sulfation degree of the starting material after the first oxidation step is determined on a sample of the glycosaminoglycan intermediate obtained by the first oxidation step (a), after reduction by $NaBH_4$.

Preferably, the glycosaminoglycan derivatives of the present invention derive from natural or synthetic (chemically or enzymatically obtained) glycosaminoglycans, more preferably from 2-O- and/or 2-N-desulfated glycosaminoglycans. In a preferred embodiment, said natural or synthetic glycosaminoglycan is unfractionated heparin, LMWH, or heparan sulfate, optionally 2-O- and/or 2-N-desulfated.

More preferably the glycosaminoglycan derivatives derive from natural or synthetic heparins or LMWHs, 2-O- and optionally 2-N-desulfated.

As an example, heparin chains can naturally comprise from about 5% to 35% of 2-O-non-sulfated uronic acid residues, from 0% to 50% of N-acetylated glucosamine residues and from about 0% to 6% of N-unsubstituted (neither N-sulfated, nor N-acetylated) glucosamine residues. Different sulfation degree depends on the heparin source (animal species, organ sources) and on the extraction procedures. Every 2-O- or 2-N-non-sulfated residue of glycosaminoglycans, not bearing 3-0-sulfate substituents, is susceptible of oxidation with ring opening (split) and conversion of vicinal diols and $OH/NH_2$ to aldehydes. Optionally, graded 2-O-desulfation of the starting glycosaminoglycans allows to modulate the ratio of glucosamine/uronic acid split residues.

The invention further relates to the process for preparing said carboxylated glycosaminoglycan derivatives and further to their use as active ingredients of medicaments for treating pathological conditions, either as sole active ingredient or in combination with other medicaments. Said pathological conditions comprise multiple myeloma and other neoplastic diseases, including their metastatic forms. Furthermore, the invention relates to said carboxylated glycosaminoglycan derivatives for use in any therapeutic indication gaining benefit from inhibition of heparanase. The invention also relates to pharmaceutical compositions containing said carboxylated glycosaminoglycan derivatives, optionally in combination with at least one further active ingredient.

The process for preparing the carboxylated glycosaminoglycan derivatives of the invention comprises: oxidation, preferably by periodate (or by use of oxidizing reagents having similar reactivity), of the susceptible non-sulfated residues of a glycosaminoglycan, under conditions effective to convert adjacent diols and optionally adjacent $OH/NH_2$ to aldehydes, followed by oxidation of the glycosaminoglycan resulting from the first oxidation, under conditions to obtain two new carboxylate groups from the corresponding aldehyde groups.

The process of the present invention thus comprises the oxidation, preferably by periodate, of 10% to 100%, preferably of from 25% to 100%, of 2-O- and optionally 2-N-, 3-O-non-sulfated residues of a glycosaminoglycan, under conditions effective to convert adjacent diols and optionally adjacent $OH/NH_2$ to aldehydes; then it comprises the oxidation of the oxidized glycosaminoglycan under conditions effective to convert said dialdehydes to carboxylate groups.

Preferably, the starting glycosaminoglycan is a natural or synthetic glycosaminoglycan; more preferably it is selected from heparin, low molecular weight heparins, or heparan sulfate; most preferably it is selected from heparin and LMWHs, 2-O- and optionally 2-N-desulfated.

Preferably, the starting glycosaminoglycan has a sulfation degree ($SO_3$—/COO—) of from 0.8 to 2.8, more preferably of from 0.9 to 2.5, by conductimetric titration, as defined herein.

The first oxidation of the inventive process is preferably carried out at a pH of from 3 to 10, more preferably at a pH of from 4.5 to 8. In a preferred embodiment the first oxidation of the inventive process is carried out at a pH of from 3 to 5, in order to cleave only the linkage $C_2$-$C_3$ of the non-sulfated uronic acid residues, avoiding side reactions. In another preferred embodiment, the first oxidation of the inventive process is carried out at a pH of from 5.5 to 10, in order to cleave the linkage $C_2$-$C_3$ of both the 2-O-non-sulfated uronic acid and N-non-sulfated glucosamine residues.

In a preferred embodiment, the first oxidation is performed under conditions to cleave the bond between the C2 and C3 of both the 2-O-non-sulfated uronic acids and of the 2-N-, 3-O-non-sulfated glucosamines.

Optionally, the inventive process is performed in the presence of NTA (nitrilotriacetic acid), a chelating and sequestering agent used to reduce depolymerization, in the presence of $NaHCO_3$ or pyridine, to alkalinize the reaction solution, or in the presence of $MnCl_2$ with or without NTA. The further dialdehyde oxidation is preferentially performed using NaClO$_2$, or by the use of agents with comparable oxidizing properties, such as TEMPO (2,2,6,6 Tetra Methyl-1-Piperidinyl-Oxy).

Preferably, carboxylated uronic acid residues in the glycosaminoglycans derivatives of the present invention are from 25% to 100%, more preferably from 50% to 100%, most preferably from 60% to 90%, of the total residues of the total carboxylated residues of the glycosaminoglycan.

The carboxylated glycosaminoglycan derivatives obtainable by the above processes preferably have a molecular weight of from 8000 to 30,000 Da., depending on the process conditions and on the starting glycosaminoglycan employed. In a preferred embodiment, more preferably when unfractionated heparin is employed as the starting glycosaminoglycan, the carboxylated glycosaminoglycan derivative obtainable by the above processes preferably has a molecular weight of from 3,000 to 20,000 Da., preferably from 3,500 to 12,000 Da.

The novel glycosaminoglycan derivatives obtainable by the process of the present invention represent a new class of heparin-like polysaccharides, characterized by the presence of split residues, each bearing two additional carboxylate groups. Note that residues bearing one natural carboxylate group, are converted to tricarboxylated residues by the process of the present invention. Said novel di/tricarboxylated glycosaminoglycan derivatives have unexpectedly shown to be strong heparanase inhibitors in vitro and to inhibit myeloma in animal models.

Glycosaminoglycan derivatives comprising residues bearing two or three carboxylate groups, being also less sulfated than the parent glycosaminoglycan, display more favorable pharmacokinetics than their analogues bearing less carboxylic groups.

The present invention further relates to the compounds obtainable by the above processes for use as medicaments.

In particular, the present invention relates to the compounds obtainable by the above processes for use as antitumor, preferably for use as antimyeloma medicaments, either alone or in combination with at least one further active ingredient.

Heparin and low molecular weight heparin derivatives prepared according to the present invention have shown effective inhibition of heparanase activity, both in vitro and in vivo in a multiple myeloma experimental model.

EXAMPLES

Compounds Preparation

Samples of unfractionated or fractioned heparins, endowed with different degree of sulfation (SO$_3^-$/COO$^-$) by conductimetric titration, were subjected to periodate oxidation (to give split dialdehyde units), performed by modification of known methods. Graded 2-O-desulfation of unfractionated heparins (UFH) was performed following modification of known methods (Jaseja M. et al., 1989, "Novel regio- and stereo-selective modifications of heparin in alkaline solution. Nuclear magnetic resonance spectroscopic evidence." Canad J Chem, 67, 1449-1455; R. N. Rej and A. S. Perlin, 1990, "Base-catalyzed conversion of the a-L-iduronic acid 2-sulfate unit of heparin into a unit of a-L-galacturonic acid and related reactions." Carbohydr. Res. 200, 25, 437-447; Casu B. et al., 2004, "Undersulfated and Glycol-Split Heparins Endowed with Antiangiogenic Activity." J. Med. Chem., 47, 838-848). Under basic conditions, 2-O-desulfated (natural or chemically induced) L-iduronic acid units are converted into 2,3-epoxy derivatives and finally to L-galacturonic acid units. The dialdehydes originated from the uronic acid units, and optionally from glucosamines, are preferably, and within a short time, further oxidized to dicarboxylates.

In Vitro Testing

Based on previous studies of Bisio et al. (Bisio A. et al. 2007, High-performance liquid chromatographic/mass spectrometric studies on the susceptibility of heparin specie to cleavage by heparanase. Sem Thromb hemost 33 488-495), heparanase inhibiting activity was determined in vitro by the group of Prof. Vlodaysky at the University of Haifa, Israel, according to the method described by Hammond et al. (Hammond et al. 2010, Development of a colorimetric assay for heparanase activity suitable for kinetic analysis and inhibitor screening. Anal. Biochem. 396, 112-6). Briefly, heparanase can cleave the synthetic pentasaccharide Fondaparinux, which is an antithrombotic drug, structurally corresponding to the antithrombin binding site of heparin. After heparanase cleavage, a trisaccharide and a reducing disaccharide are obtained. The latter can be easily quantified in order to assess heparanase activity. In the present examples, the assay solution (100 ul) comprised 40 mM sodium acetate buffer pH 5.0 and 100 mM Fondaparinux (GlaxoSmithKline), with or without inhibitor sample. Heparanase was added to a final concentration of 140 pM to start the assay. The plates were sealed with adhesive tape and incubated at 37° C. for 2-24 hours. The assay was stopped by addition of 100 μL of a solution of 1.69 mM 4-[3-(4-iodophenyl)-1H-5 tetrazolio]-1,3-benzene disulfonate (WST-1, Aspep, Melbourne, Australia) in 0.11M NaOH. The plates were resealed with adhesive tape and developed at 60° C. for 60 min. The absorbance was measured at 584 nm (Fluostar, BMG, Labtech). In each plate, a standard curve constructed with D-galactose as the reducing sugar standard was prepared in the same buffer and volume over the range of 2 to 100 μM. The IC$_{50}$ value was determined. Because this assay has a homogeneous substrate with a single point of cleavage, the kinetics and biochemical parameters of the enzyme can be reliably characterized. Results obtained using the above described colorimetric assay were validated using sulfate labeled extracellular matrix (ECM) as substrate. Briefly, the ECM substrate is deposited by cultured corneal endothelial cells and hence closely resembles the subendothelial basement membrane in its composition, biological function and barrier properties. Detailed information about the preparation of sulfate labeled ECM and its use for the heparanase assay can be found in: Vlodaysky, I., Current Protocols in Cell Biology, Chapter 10: Unit 10.4, 2001. The assay is highly sensitive, better resembles the in vivo conditions, but, due to its biological nature, it is semi-quantitative and limited in terms of biochemical parameters.

In Vivo Testing

The antimyeloma activity in vivo was tested substantially following the procedure described in Yang Y et al. (Yang Y., et al. 2007, The syndecan-1 heparan sulfate proteoglycan is a viable target for myeloma therapy. Blood 110:2041-2048). Briefly, CB17 scid/scid mice aged 5 to 6 weeks were obtained from Arlan (Indianapolis, Ind.) or Charles River Laboratories (USA). Mice were housed and monitored in the animal facility of the University of Alabama at Birmingham. All experimental procedures and protocols were approved by the Institutional Animal Care and Use Committee. 1×10$^6$ heparanase-expressing CAG myeloma cells (high or low expressing) were injected subcutaneously into the left flank of each mouse. Ten days after injection of tumor cells, mice were implanted with Alzet osmotic pumps (Durect Corporation, Cupertino, Calif.) on the right flank. Pumps contained either solution of test compounds (new heparin derivatives)

or PBS as control. The solution was delivered continuously for 14 days. After 14 days, the animals were killed and the wet weight of the subcutaneous tumors and the mean sera kappa level were assayed and compared among the experimental groups by log-rank test (p<0.05 was considered statistically significant).

Weekly luciferase bioluminescence imaging provides quantitative data on primary tumors and tracks metastasis within bone as well as soft tissues. Notably, the SCID-hu model is unique in that human tumor cells are injected directly into small pieces of human fetal bone implanted subcutaneously in SCID mice, thus closely recapitulating human myeloma.

General Procedure of NMR Analysis

Spectra were recorded at 25° C. on a Bruker Avance 500 spectrometer (Karlsruhe, Germany) equipped with a 5-mm TCI cryoprobe or with a 10 mm BBO probe. Integration of peak volumes in the spectra was made using standard Bruker TopSpin 2.0 software. The structure of dicarboxylated uronic acid residues was determined by two-dimensional heteronuclear experiments that confirmed the presence of the tricarboxylate residues and permitted the identification of their chemical shift. In the table below the assigned chemical shifts of proton and carbons in position 1, 4, 5 of the dicarboxylated residue, of glucosamine and 2-O-sulfated iduronic acid are reported.

| Signals corresponding to residue position | $^1$H ppm | $^{13}$C ppm |
|---|---|---|
| C5-Uronic acid gsox | 4.97 | 81.65 |
| C4-Uronic acid gsox | 4.59 | 81.22 |
| C1-Uronic acid gsox | 5.01 | 103.71 |
| C4 | 3.63 | 79.14 |
| C1-Glucosamine NS (ANS) | 5.40 | 99.17 |
| C1-ANS linked to (gsox) | 5.03 | 100.19 |
| C1-Iduronic acid 2S | 5.17 | 102.11 |

General Procedure for Calculation of Carboxyl Groups Increment

The increase of carboxyl groups in the uronic acid residues of dicarboxylated heparin derivatives was calculated starting from respective values of molar ratio $SO_3^-/COO^-$ of the starting material (unfractionated heparin or at least partially desulfated heparins and LMWHs) and of the dicarboxylated derivatives, evaluated by conductimetric titration (Casu B. and Gennaro U., 1975, Carbohydr Res 39, 168-176). In particular, the sulfation degree of the starting material is determined after the first oxidation step, on a reduced sample of the glycosaminoglycan oxidized intermediate (see examples 4-7), while the sulfation degree of the final glycosaminoglycan carboxylated derivative is determined after the second oxidation step (see examples 8-11, 13-14).

$SO_3^-/CO_2^-=A$ (ratio in starting materials) $SO_3^-=A/CO_2^-$
$SO_3^-/CO_2^-=B$ (ratio in dicarboxylated derivatives) $SO_3^-=B/CO_2^-$ Given that the number of sulfate groups does not change during the two steps of oxidation, it can be concluded that the increase of the carboxyl groups ($CO_2^-{}_{(dicarboxylated\ derivatives)}/CO_2^-{}_{(starting\ materials)}$) is equal to the ratio of the individual molar ratios A and B.

Carboxyl increment (C.I.)=AB=
$CO_2^-{}_{(dicarboxylated\ derivatives)}/CO_2^-{}_{(starting\ materials)}$.

Enzymatic Cleavage of Heparins and their Carboxylated Derivatives and HPLC/MS Analysis The substrate (2-3 mg) was dissolved in a 1:1 (v/v) mixture of 100 mM sodium acetate buffer (pH 7.0) and 10 mM calcium acetate to obtain a 7.7 mg/ml solution. To carry out the enzymatic cleavage 144 µl of the mixture of 100 mM sodium acetate and 10 mM calcium acetate (1:1) and 3 µl of heparinases mixture (heparin lyases I, II and III) (1 µl of each lyase, 2 mU/µl enzyme solution) were added to 13 µl of the heparin solution. The reaction mixture was stirred at 37° C. (Thermo-Shaker TS-100, Biosan) for 24 h. The reaction was stopped by adding 3 µl of 3% HCOOH. Each sample was diluted two times with water and analyzed by IPRP-HPLC/ESI-TOF (micrOTOF-Q, Bruker). A C18 kinetex and a gradient (0'-17% B, 15'-20% B, 55'-40% B, 100' 50% B, 115' 90% B) that use fase A (pH 6.25) and B (pH 7.95) with 10 mM DBA-CH$_3$COOH was used with a flow rate 100 µL/min.

Example 1 (G7669)

A sample of UFH (2.5 g of lot. G5842) in 1M NaOH (32 ml) was heated at 60° C. for 30 min. After cooling at room temperature and neutralization with 2N HCl, the solution was dialyzed at room temperature for 3 days against distilled water in membranes (cut-off: 3500 Da). Concentration under reduced pressure and freeze drying gave: 2.15 g (yield=80% w/w) of an intermediate with 13% of the total uronic acid residues bearing epoxide group as determined by $^{13}$C-NMR. The sample was then dissolved in water (32 ml) and kept under stirring at 70° C. for 2 days, in order to hydrolyze the epoxy groups. After concentration and freeze-drying, G7669 was obtained.

Example 2 (G8661)

A sample of UFH (2.11 g of lot. G3378) in 27 ml of 1N NaOH was stirred at 60° C. for 30 min. Neutralization, cooling at room temperature and dialysis, concentration and freeze-drying (as described in Example 1) gave the intermediate G8637 (1.5 g). Since its $^{13}$C-NMR spectrum indicated the presence of epoxy groups, G8637 (1.5 g) was dissolved in water (32 ml) and kept under stirring at 70° C. for 2 days, in order to hydrolyze the epoxy groups. After concentration and freeze-drying, G8661 was obtained (1.5 g).

Example 3 (G8699)

A sample of UFH (2.01 g of lot. G3378) was processed as described in Example 2 to give the intermediate epoxy-containing derivative G8638. A sample of G8638 (1.4 g) was dissolved in water (32 ml) and heated under stirring at 70° C. for 24 hours, to give, after concentration and freeze-drying, 1.3 g of G8699.

Periodate Oxidation of Unfractionated Heparin and 2-O-Desulfated Derivatives

Example 4 (G7731)

Starting from sample G7669 of Example 1 (1.8 g, 13% 2-O-desulfation) in water (52 ml), the solution was cooled at 4° C., stirred in the dark and 52 ml of 0.2M NaIO$_4$ were added. After 16 hours, the excess of periodate was quenched by adding ethylene glycol (5.2 ml) and after 1 hr. at 4° C. the reaction mixture was desalted by dialysis at 4° C. for 16 hours. After concentration under reduced pressure and freeze-drying, the dialdehyde-bearing G7731 was obtained (1.5 g), yield=83%. A small portion of sample was reduced with NaBH$_4$ to measure MW=8,242 Da and SO$_3^-$/COO$^-$=2.46, by conductimetric titration.

Example 5 (G8425)

Starting from a sample of UFH (0.25 g, lot. G3378) and following the same procedure described in Example 4, the dialdehyde-bearing G8425 was obtained (0.24 g), yield=96% w/w.

Example 6 (G8678)

Starting from a sample of G8661 of Example 2 (1.5 g) and performing the same procedure described in Example 4, the dialdehyde-bearing G8678 was obtained (1.5 g). A small portion of sample was reduced with NaBH$_4$ to measure SO$_3^-$/COO$^-$=1.96 by conductimetric titration.

Example 7 (G8710)

Starting from a sample of G8699 of Example 3 (0.56 g) and following the same procedure described in Example 4, the dialdehyde-bearing G8710 was obtained (0.56 g). A small portion of sample was reduced with NaBH$_4$ to measure SO$_3^-$/COO$^-$=1.51 by conductimetric titration.

Oxidation of the Dialdehydic Uronic Acid Intermediates to the Corresponding Dicarboxylates

Example 8 (G7927)

A sample of G7731 of Example 4 (0.3 g) was dissolved in water (29 ml), cooled at 0° C. in a double-necked round-bottomed flask and, under stirring in nitrogen atmosphere, it was treated with an aqueous solution (6 ml) containing NaClO$_2$ (0.362 g). After a drop-wise addition of glacial acetic acid (0.118 ml) up to reach pH 4.0, the reaction mixture was stirred at room temperature for 24 hours. After further 3 hours under stirring at room temperature, by fluxing N$_2$, a colorless solution was obtained. The reaction mixture was neutralized with 0.5N NaOH and desalted by dialysis as described in Example 4. Concentration and freeze-drying gave G7927 (0.228 g), yield=76% w/w, having:
MW=6,450 Da;
SO$_3^-$/COO$^-$=1.23;
Carboxyl increment (C.I.)=2
In vitro heparanase inhibition analysis gave: IC$_{50}$=10 ng/ml.

Example 9 (G8437)

Starting from a sample of G8425 of Example 5 (0.25 g), in which only the non-sulfated uronic acids naturally present in the chain of heparin (18%) were oxidized following the same procedure described in example 8, G8437 (0.21 g) was obtained by reducing to 1.5 hours the N$_2$ fluxing before neutralization of the reaction mixture, having:
MW=12,100 Da;
SO$_3^-$/COO$^-$=1.62;
Carboxyl increment (C.I.): 1.43.
In vitro heparanase inhibition analysis gave: IC$_{50}$=10 ng/ml.

Example 10 (G8767)

Starting from samples of G8678 of Example 6 (1 g) and following the procedure described in Example 8, G8767 (1.05 g) was obtained, having:
MW=8,800 Da;
SO$_3^-$/COO$^-$=1.27;
Carboxyl increment (C.I.)=1.55.
In vivo antimyeloma activity analysis (60 mg/kg day for 14 days) gave: 52% tumor inhibition and 20% serum K inhibition.

Example 11 (G8733)

Starting from sample G8710 of Example 7 (0.56 g) and following the procedure described in the Example 8, G8733 (0.453 g) was obtained, yield=80% w/w, having:
MW=5,540 Da;
SO$_3^-$/COO—=0.97;
Carboxyl increment (C.I.)=1.56.
In vivo antimyeloma activity analysis (60 mg/kg day for 14 days) gave: 53% tumor inhibition.

Example 12 (G9685)

Starting from a sample of UFH (lot G3378) and following the procedure described in Example 4, the dialdehyde derivative was obtained. The dialdehyde derivative was further oxidized in the presence of sodium chlorite, following the procedure of Example 8, obtaining the carboxylated derivative G9685, MW=11,700 Da.
In vitro heparanase inhibition analysis gave: IC$_{50}$=10 ng/ml;
In vivo antimyeloma activity analysis (60 mg/kg day for 14 days) gave: 68% tumor inhibition.

Example 13 (G7897)

A sample of G7731 of Example 4 (0.3 g) dissolved in water (3 ml) and treated with 1.36 ml of NaClO$_2$ to pH 8.2-8.5 with HCl 4%. Then 1 mg of TEMPO was added and pH was maintained a 7-7.5 with NaOH 1M for 24 hours. The reaction mixture was desalted by dialysis, concentrated and freeze-dried to give G7897 (0.190 g), yield=63% w/w, having:
SO$_3^-$/COO$^-$=1.92;
Carboxyl increment (C.I.)=1.28.

Example 14 (G9585)

Starting from a sample of 2-O-desulfated heparin (G9416, SO$_3^-$/COO$^-$=1.39), following the procedure described in Example 4, the dialdehyde derivative G9577 was obtained. A sample of G9577 (0.242 g) dissolved in water (21 ml) was cooled at 0° C. in a double-necked round-bottomed flask and, under stirring in nitrogen atmosphere, it was treated with an aqueous solution (1 ml) containing NaClO$_2$ (0.128 g). After a drop-wise addition of glacial acetic acid (0.084 ml) up to reach pH 4.0, the reaction mixture was stirred at room temperature for 24 hours. After further 3 hours under stirring at room temperature, by fluxing N$_2$, a colorless solution was obtained. The reaction mixture was neutralized with 0.5N NaOH and desalted by dialysis as described in Example 4. Concentration and freeze-drying gave G9585 (0.148 g), yield=61% w/w, having:
MW=4,700 Da;
SO$_3^-$/COO$^-$=0.82;
Carboxyl increment (C.I.)=1.69.
In vitro heparanase inhibition analysis gave: IC$_{50}$=44 ng/ml.

What is claimed is:

1. Carboxylated derivatives of glycosaminoglycan, the carboxylated derivative chain comprising the dimeric sugar moiety (I) but not dimeric sugar moiety (II) or (III):

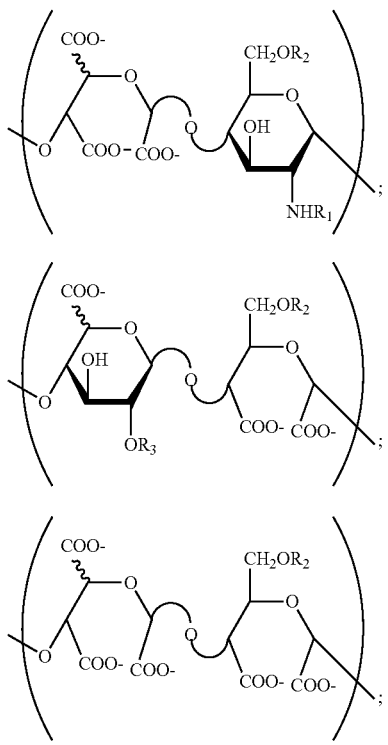

wherein $R_1$ is $SO_3$ or Ac; $R_2$ is $SO_3$ or H; $R_3$ is H or $SO_3$; wherein the glycosaminoglycan is selected from unfractionated heparin, low molecular weight heparin and heparan sulfate wherein the glycosaminoglycan has a sulfation degree ($SO_3^-/COO^-$), determined by conductometric titration as defined herein, of from 0.8 to 2.8.

2. Carboxylated derivatives of glycosaminoglycan, the carboxylated derivative chain comprising dimeric sugar moieties (I), (II) and (III):

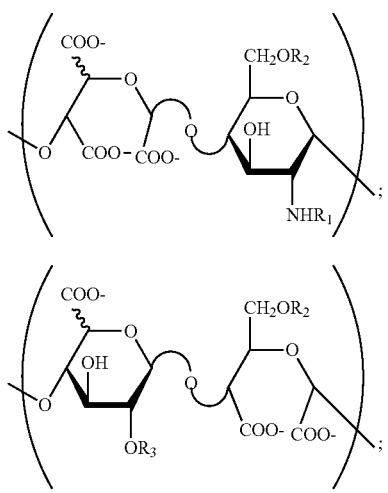

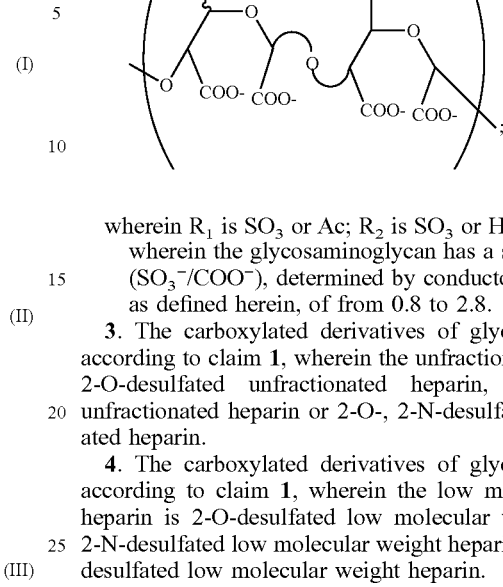

wherein $R_1$ is $SO_3$ or Ac; $R_2$ is $SO_3$ or H; and $R_3$ is $SO_3$ wherein the glycosaminoglycan has a sulfation degree ($SO_3^-/COO^-$), determined by conductometric titration as defined herein, of from 0.8 to 2.8.

3. The carboxylated derivatives of glycosaminoglycan according to claim 1, wherein the unfractionated heparin is 2-O-desulfated unfractionated heparin, 2-N-desulfated unfractionated heparin or 2-O-, 2-N-desulfated unfractionated heparin.

4. The carboxylated derivatives of glycosaminoglycan according to claim 1, wherein the low molecular weight heparin is 2-O-desulfated low molecular weight heparin, 2-N-desulfated low molecular weight heparin or 2-O-, 2-N-desulfated low molecular weight heparin.

5. The carboxylated derivatives of glycosaminoglycan according to claim 1, wherein the carboxylated derivatives of glycosaminoglycan have a sulfation degree ($SO_3^-/COO^-$), determined by conductimetric titration as defined herein, of from 0.82 to 1.92.

6. The carboxylated derivatives of glycosaminoglycan according to claim 1, wherein the carboxylated derivatives have a molecular weight of from 3,000 to 20,000 Da.

7. The carboxylated derivatives of glycosaminoglycan according to claim 1, wherein the carboxylated derivatives have a molecular weight of from 3,500 to 12,000 Da.

8. A method of treating a disease gaining benefit from inhibition of heparanase, comprising administering to a human in need of such treatment a pharmaceutical composition comprising a therapeutically effective amount of the carboxylated derivatives of glycosaminoglycan of claim 1, wherein the disease is diabetic nephropathy, inflammatory bowel disease, colitis, arthritis, psoriasis, sepsis, atherosclerosis or tumor.

9. A method of treating tumor metastasis or a tumor in a human, the method comprising administering to the human in need of such treatment a pharmaceutical composition comprising a therapeutically effective amount of the carboxylated derivatives of glycosaminoglycan of claim 1.

10. The method according to claim 9, wherein the tumor is myeloma.

11. The carboxylated derivatives of glycosaminoglycan according to claim 2, wherein the unfractionated heparin is 2-O-desulfated unfractionated heparin, 2-N-desulfated unfractionated heparin or 2-O-, 2-N-desulfated unfractionated heparin.

12. The carboxylated derivatives of glycosaminoglycan according to claim 2, wherein the low molecular weight heparin is 2-O-desulfated low molecular weight heparin, 2-N-desulfated low molecular weight heparin or 2-O-, 2-N-desulfated low molecular weight heparin.

13. The carboxylated derivatives of glycosaminoglycan according to claim 2, wherein the carboxylated derivatives of glycosaminoglycan have a sulfation degree ($SO_3^-/COO^-$), determined by conductimetric titration as defined herein, of from 0.82 to 1.92.

14. The carboxylated derivatives of glycosaminoglycan according to claim 2, wherein the carboxylated derivatives have a molecular weight of from 3,000 to 20,000 Da.

15. The carboxylated derivatives of glycosaminoglycan according to claim 2, wherein the carboxylated derivatives have a molecular weight of from 3.500 to 12,000 Da.

16. A method of treating an indication gaining benefit from inhibition of heparanase, comprising administering to a human in need of such treatment a pharmaceutical composition comprising a therapeutically effective amount of the carboxylated derivatives of glycosaminoglycan of claim 2, wherein the indication is diabetic nephropathy, inflammatory bowel disease, colitis, arthritis, psoriasis, sepsis, atherosclerosis or tumor.

17. A method of treating tumor metastasis or a tumor in a human, the method comprising administering to the human in need of such treatment a pharmaceutical composition comprising a therapeutically effective amount of the carboxylated derivatives of glycosaminoglycan of claim 2.

18. The method according to claim 17, wherein the tumor is myeloma.

\* \* \* \* \*